Aug. 18, 1942. E. W. ROOT Plant Pat. 540
WHITE FREESTONE PEACH TREE
Filed Sept. 30, 1940
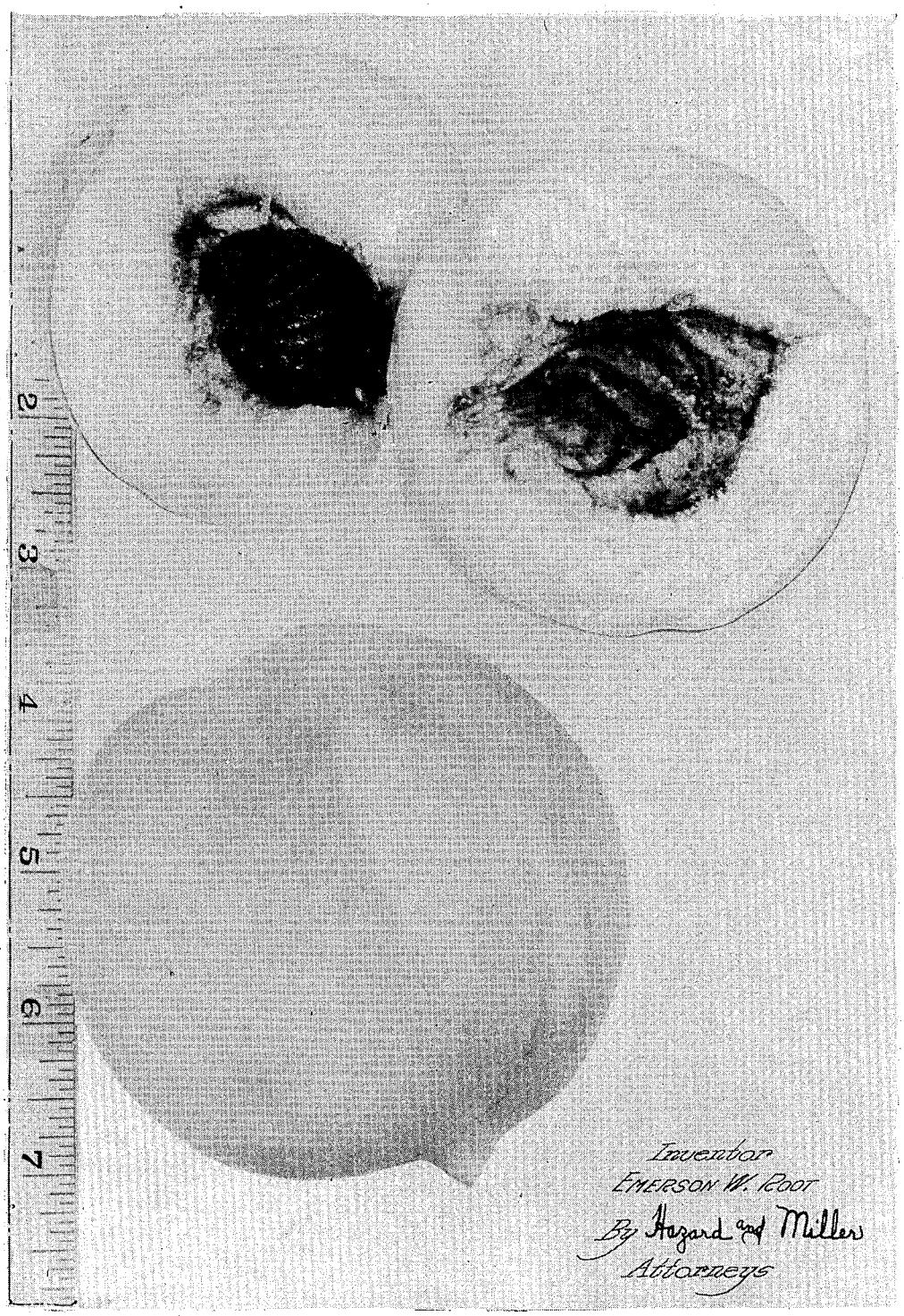

Patented Aug. 18, 1942

Plant Pat. 540

UNITED STATES PATENT OFFICE

540

WHITE FREESTONE PEACH TREE

Emerson W. Root, McFarland, Calif.

Application September 30, 1940, Serial No. 359,108

1 Claim. (Cl. 47—62)

My invention relates to a new variety of peach tree of the white freestone type. As peach trees are mainly cultivated commercially for the fruit, the chief characteristics of my improved peach tree relate to the fruit and the time of ripening compared with other white freestone types of peaches. The white freestone peach has long enjoyed a good reputation and popularity with the consumers as a high grade type of peach particularly suitable for eating as a fresh fruit but it also is a good fruit for preserving and to a certain extent is a good type of shipping fruit. However in most localities the ripening and hence the merchandising season of the white freestone peach is of quite short duration and is mainly in the early summer, this being particularly true in California.

The development of my new fruit as far as I can ascertain is substantially as follows: In 1926 Mr. LeRoy Wolfe operated an orchard ranch on Peterson Road about three miles west of Highway 99 near the town of McFarland, Kern County, California. In this year Mr. Wolfe planted an acreage of Sims clingstone peaches budded on peach root trees. When the trees on this acreage planted by Mr. Wolfe bore fruit, one tree bore white freestone peach fruit instead of the yellow clingstone. I judge that the clingstone bud had not developed or had been broken off and a shoot had grown from the root stock making the variety a seedling. In 1931 buds were taken from this tree bearing white freestone peach fruit and budded into apricot seedling trees. These latter trees, thirteen in number, were planted in my orchard in 1932, this being located on my ranch near the town of McFarland, Kern County, California. These thirteen trees have been bearing white freestone fruit consistently for four or five years and such fruit and the characteristics of the trees are as herein described. I have since budded about 100 more of this white freestone type on apricot tree root but these are not yet of bearing age. The original tree cannot now be examined as the original trees of the Sims clingstone variety planted by Mr. Wolfe were removed with the rest of the orchard. My budded trees and plantings have been stabilized and have the characteristics herein detailed. The white freestone peach of my invention is comparable to the Hale freestone yellow peach which is noted as an excellent peach for eating fresh and of a large size. The pulp also has certain characteristics similar to the Hale in regard to the firmness, the good keeping qualities and is fully as juicy as the Hale.

In order to identify and distinguish this variety of peach from other peaches the following information is supplied in answer to the Description blank for peaches in Hedrick's "Systematic Pomology," edition of 1925, pages 130 and 131. The tree is of medium size, vigorous, upright to spreading open and vase-formed. It is hardy under California conditions and may be described as productive and as a regular bearer. The trunk is of medium size and of medium smoothness. The branches are of medium size and are of medium smoothness having a brown color. The lenticels are numerous and small. The leaves are of medium length and of medium thickness. The glands average four in number are opposite medium reniform and green. Their positions are two on the petiole and two on the base of the leaf blade. There are no stipules. Flower buds may be described as hardy of medium size and of medium length. They are plump, free, and pubescent. The flowers bloom between February 25 and March 5 and may be described as early to medium. They are of medium size and pink to rosolane at the margin. The leaves average about six and one-half inches in length and one and one-half inches in width. They are medium wavy, lanceolate, acutely pointed of medium thickness and medium green. They are smooth and have a crenate margin. The fruit may be described as follows. The skin is medium thick and medium tough, and semi-free. The flesh is creamy white, juicy, fine-grained and mildly subacid. The quality is very good. The stone is free, medium to large, flattened, and obovate. The fruit ripens about August 15 (or a little past mid-season). The keeping quality and shipping quality are both good. The average length of fruit is three and one-quarter inches with the greatest diameter three and one-quarter inches. The fruit is slightly irregular and runs from medium to above medium. It is roundish oval and the halves are slightly unequal. The cavity is medium as to depth and width. It is regular and abrupt. The suture is shallow and distinct. The apex is short tipped. The color of the fruit is creamy white and blushed on exposed surface with a slight carmine strip. The color of the pit is brown with a reddish tinge, blunt, pitted, and furrowed at the apex. The use of the peach is for dessert, market, and home use. The pubescence is medium as to length and thickness. In adjoining localities to where my fruit ripened on August 15, Nectar peaches ripened on June 7; Babcock peaches ripened July 5; Elberta peaches ripened July 20, and J. H. Hale peaches ripened July 25.

In the illustration of my invention accompanying this specification, as the peach tree has been developed for its fruit and the fruit in the ripened condition is the chief characteristic difference from other white freestone peaches, the illustration is a photograph of the fruit only of the peach tree plant. Such photograph taken with the fruit resting on a horizontal surface at a substantially vertical line of camera sight illustrates the fruit in comparison with a measuring rule graduated in inches. It depicts one peach uncut and another peach severed in the diametrical plane of the suture showing one-half with the flesh exposed and with the pit retained and the other half with the pit cavity.

In these photographs and illustrations the fruit was somewhat over-ripe for shipping but substantially in excellent condition for eating as a fresh fruit. Fruit picked for shipment would be materially less ripened. The photograph of the whole fruit depicts the suture line remote from the scale, this having a greenish tinge of color. The opposite side adjacent the rule has a pink flesh typical of this and other peaches. The skin has a complete covering of fine peach bloom.

The cut and open fruit as shown has a distinct white color flesh between the pit cavity and the skin, this being substantially the same degree of whiteness as other white freestone peaches. The cavity formed by the pit is of a typical reddish color as in other white freestone peaches. Due to the fact that the peach when cut was very juicy, the moisture produced highlights on the half of the cut peach having the cavity exposed.

As above mentioned, one of the characteristic differences of this peach and other white freestone peaches is in the size of the fruit when mature, it being considerably larger as to the average fruit from trees of substantially equivalent size and degree of bearing. The meat of the fruit is firmer than other white freestone peaches but due to the increased size has much more juice. To the taste the fruit is slightly sweeter with the rich peach flavor than most other white freestone peaches.

One of the characteristic features of my new peach which cannot be shown in the illustrations is its later maturing in the district in which I have grown the same than other well known white flesh freestone peaches, the time of full ripening for marketing as fresh fruit being from 3 to 4 weeks after other white freestone peaches are off the market.

I claim:

A new variety of white freestone peach tree characterized by the peach fruit when mature and ripe having a medium thick and medium tough skin, a creamy white, juicy, fine-grain, mildly acid flesh and having a stone that is medium to large, flattened and obovate, ripening a little past mid-season about forty days after the Babcock; twenty-five days after the Elberta; and twenty days after the J. H. Hale peach grown in the same climatic conditions and under similar cultivation procedures, the flowers blooming from hardy medium, plump free pubescent buds from February 25 to March 5, and being of medium size and pink to rosolane at the margin as herein disclosed.

EMERSON W. ROOT.